United States Patent [19]

Murray

[11] Patent Number: 4,537,966

[45] Date of Patent: Aug. 27, 1985

[54] 1-(AMINOBENZOYL)-1H-INDAZOL-3-OLS

[75] Inventor: Robert J. Murray, Penfield, N.Y.

[73] Assignee: Pennwalt Corporation, Philadelphia, Pa.

[21] Appl. No.: 564,540

[22] Filed: Dec. 22, 1983

[51] Int. Cl.$^3$ .................. C07D 231/56; C07D 471/04
[52] U.S. Cl. ..................... 546/120; 548/359; 548/372
[58] Field of Search ............ 548/359, 372, 371; 546/120

[56] References Cited

U.S. PATENT DOCUMENTS

| | | | |
|---|---|---|---|
| 3,238,201 | 3/1966 | Scherrer | 544/90 |
| 3,470,194 | 9/1969 | Palazzo | 424/273 N |
| 3,925,388 | 12/1975 | Hoehn et al. | 546/120 |
| 4,171,446 | 10/1979 | Wiedemann et al. | 548/372 |

OTHER PUBLICATIONS

Palazzo, J. Med. Chem., vol. 9, pp. 38–41, (1966).
Janssen, Int'l Meetings on Mol. Spec. Proceed., vol. 2, pp. 820–831, (1959).
Hardtmann, J. Het. Chem., vol. 12, pp. 565–572, (1975).
Chem. Abst. 86, 121242q, (1977).

Primary Examiner—Richard A. Schwartz
Assistant Examiner—Kurt G. Briscoe

[57] ABSTRACT

Aminobenzoyl-1H-indazol-3-ols which are useful as immunomodulators and in controlling inflammation in warm-blooded animals are prepared.

18 Claims, No Drawings

1-(AMINOBENZOYL)-1H-INDAZOL-3-OLS

BACKGROUND OF THE INVENTION

This invention relates generally to novel 1H-indazol-3-ols and more specifically to 1-(aminobenzoyl)-1H-indazol-3-ols having pharmaceutical properties.

1-substituted-3-(2,3-dihydroxy propoxy)indazoles are disclosed in U.S. Pat. No. 3,726,896, 1-substituted 3-dimethylaminoalkoxy-1H-indazoles are disclosed in a paper by G. Palazzo et al., *J. Med. Chem.*, 9, 38 (1966), and (1-substituted indazol-3-yl)oxyalkanaoic acids are disclosed in U.S. Pat. No. 3,470,194 as anti-inflammatory agents. In each instance substitution at the 1 position of indazole is limited to H, aryl, and arylalkyl. Furthermore, 3-substitution appears to be important for the reported anti-inflammatory activity. 1-Benzoyl-1H-indazol-3-ol is disclosed by R. Janssen, *Int'l. Meetings on Mol. Spec. Proced*, 2, 820 (1959); CA 59 356d, however, no pharmacology has been reported. I have found 1-benzoyl-1H-indazol-3-ol to be minimally effective in the carrageenan induced paw edema model at 50 m/k; a result which is far inferior to the 1-(o-aminobenzoyl-1H-indazol-3-ols) of this invention.

BRIEF SUMMARY

In accordance with this invention there are provided 1-(aminobenzoyl)-1H-indazol-3-ols, and pharmaceutically acceptable salts thereof, represented by the following formula:

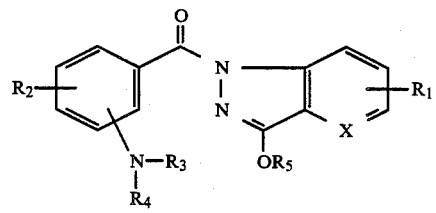

in which $R_1$ and $R_2$ are independently selected from the group consisting of H, lower alkyl, alkoxy, hydroxy, amino, nitro, and halogen, $R_3$ is selected from the group consisting of H, lower alkyl, cycloalkyl, aryl, substituted aryl, heteroaryl, and benzyl, $R_4$ and $R_5$ are independently selected from H and lower alkyl, and X is CH or N.

Lower alkyl groups preferably contain from 1 to about 4 carbon atoms, cycloalkyl groups preferably contain from 3 to about 7 carbon atoms, and halogen is preferably chlorine or bromine. Representative compounds of this invention are 1-(o-aminobenzoyl)-1H-indazol-3ol and 1-(o-methylaminobenzoyl)-1H-indazol-3-ol.

Also provided are processes for preparing the compounds of the invention.

DETAILED DESCRIPTION

The compounds of the invention can be prepared by several methods. Primarily they are prepared from the action of an N-substituted isatoic anhydride on 1H-indazol-3-ols which are in turn prepared by the action of sodium nitrite and a reducing agent, such as sodium sulfite or sulfur dioxide, on an appropriately substituted anthranilic acid (Procedure A). The N-substituted isatoic anhydrides are prepared from isatoic anhydride and an alkylating agent such as an alkyl iodide. Alternately, the compounds of the invention can be prepared by the action of a nitrobenzoyl chloride on the indazol-3-ols followed by reduction (Procedure B). The ether derivatives are prepared either by treatment of an alkoxy indazol with isatoic anhydrides (Procedure A) or by alkylation of the aminobenzoyl indazol-3-ol product directly (Procedure C).

GENERAL PROCEDURES

Procedure A

Preparation of Aminobenzoyl indazol-3-ols and their ether derivatives via reaction of 1H-indazol-3-ols with substituted isatoic anhydrides The 1H-indazol-3-ol or its ether derivative dissolved or suspended in an aprotic solvent such as toluene or dimethylformamide is treated with one equivalent of an isatoic anhydride derivative. The reaction mixture is heated in an oil bath at 80°–90° C. for several hours, typically 4–16 hours, and the product isolated by evaporation followed by recystallization from aqueous ethanol.

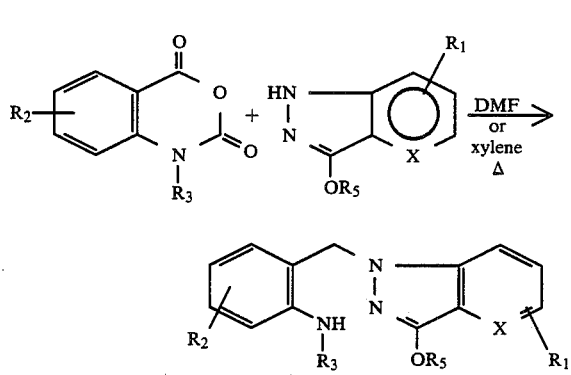

Procedure B

Preparation of Aminobenzoyl-1-indazol-3-ols via acylation of indazol-3-ols with nitrobenzoyl chlorides followed by reduction The 1H-indazol-3-ol dissolved in a solvent such as pyridine is treated with one equivalent of a nitrobenzoyl chloride. The reaction mixture is heated at elevated temperature for several hours and the product isolated by pouring the reaction mixture over ice/$H_2O$. Reduction of the resultant nitro compound over Pd/C in ethanol affords the desired 1-aminobenzoyl-1H-indazol-3-ol derivative.

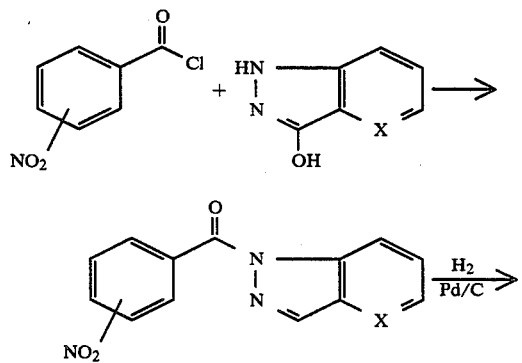

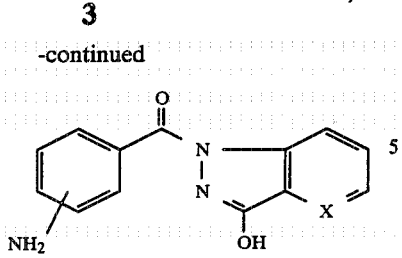

Procedure C

Preparation of 3-Alkoxy-1-aminobenzoyl-1H-indazols via alkylation of 1-aminobenzoyl-1H-indazols with alkyl halide The 1-aminobenzoyl-1H-indazol-3-ol dissolved in a solvent such as acetone is treated with one equivalent of base such as $K_2CO_3$ followed by one equivalent of an alkyl iodide and the reaction mixture is heated at an elevated temperature for several hours. The inorganic salts are filtered off, the solvent evaporated and the desired product isolated by crystallization.

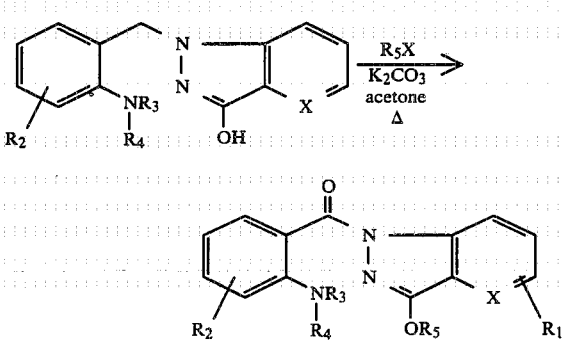

The compounds of the invention also include acid addition salts which are pharmaceutically acceptable. Acid addition salts include those derived from both organic and inorganic acids such as, for example, acetic acid, maleic acid, malic acid, fumaric acid, succinic acid, succinamic acid, tartaric acid, citric acid, lactic acid, hydrochloric acid, hydrobromic acid, hydriodic acid, sulfuric acid, phosphoric acid, and the like.

The invention is further illustrated by, but is not intended to be limited to, the following examples.

EXAMPLE 1

Preparation of 1-(o-Methylaminobenzoyl)-1H-indazol-3-ol

To 19.0 g. (0.14 mole) of 1H-indazol-3-ol dissolved in 500 ml. of dimethylformamide (DMF) was added 25.0 g. (0.14 mole) of N-methylisatoic anhydride. The resulting brown solution was heated in an oil bath at 75°–80° C. for 16 hours. The reaction mixture was allowed to cool to room temperature, and the solvent was evaporated off at reduced pressure. The residual dark oil was treated with 500 ml. ice/$H_2O$ and allowed to stand overnight. The aqueous solution was decanted from the semi-solid, and the semi-solid was dissolved in 600 ml. of hot absolute EtOH, treated with charcoal and filtered. The yellow-orange solution was diluted with $H_2O$(~50 ml.) and concentrated to ½ volume to afford 26.2 g of 1-(o-methylaminobenzoyl)-1H-indazol-3-ols as a yellow amorphous powder. Concentration of the filtrate further (½ again) yielded an additional 6.5 g of product. Total yield=31.7 g (84.7%); m.p. 164°–166° C.

Anal. Calc'd for $C_{15}H_{13}N_3O_2$: C, 67.40; H, 4.90; N, 15.72; Found: C, 67.38; H, 4.96; N, 15.72

EXAMPLE 2

Preparation of 1-(o-Ethylaminobenzoyl)-1H-indazol-3-ol

1H-Indazol-3-ol was reacted with N-ethylisatoic anhydride according to the general procedure A above and afforded the desired amine as a canary yellow solid, in 47.7% yield; m.p. 163°–165° C.

Anal. Calc'd for $C_{16}H_{15}N_3O_2$: C, 68.31; H, 5.37; N, 14.94; Found: C, 68.34; H, 5.33; N, 14.82

EXAMPLE 3

Preparation of 1-(o-Isopropylaminobenzoyl)-1H-indazol-3-ol

1H-Indazol-3-ol was reacted with N-isopropylisatoic anhydride according to the general procedure A above and afforded the desired amine as a yellow solid in 71.3% yield; m.p. 190°–192° C.

Anal. Calc'd for $C_{17}H_{17}N_3O_2$: C, 69.13; H, 5.80; N, 14.22; Found: C, 69.21; H, 5.80; N, 14.24

EXAMPLE 4

Preparation of 1-(o-Cyclohexylaminobenzoyl)-1H-indazol-3-ol

1H-Indazol-3-ol was reacted with N-cyclohexylisatoic anhydride according to the general procedure A above and afforded the desired amine as yellow solid in 20.1% yield; m.p. 150°–152° C.

Anal. Calc'd for $C_{20}H_{17}N_3O_2$: C, 17.62; H, 6.31; N, 12.53; C, 71.26; H, 6.34; N, 12.36

EXAMPLE 5

Preparation of 1-(o-Benzylaminobenzoyl)-1H-indazol-3-ol

1H-Indazol-3-ol was reacted with N-benzylisatoic anhydride according to the general procedure A above and afforded the desired amine as a yellow solid in 71.5% yield; m.p. 163°–165° C.

Anal. Calc'd for $C_{21}H_{17}N_3O_2$: C, 73.45; H, 4.99; N, 12.23; Found: C, 73.68; H, 5.04; N, 12.25

EXAMPLE 6

Preparation of 1-(o-Aminobenzoyl)-1H-indazol-3-ol

To 4.2 g. of 1(o-benzylaminobenzoyl)-1H-indazol-3-ol dissolved in 1 liter of absolute EtOH was added 1.4 g of 10% Pd/C and the mixture was hydrogenated in a Paar apparatus for 16 hrs. The catalyst was then filtered off, washed well with EtOH, and the filtrate evaporated to afford 2.3 g. of a yellow-green solid. Recrystallization from aqueous. EtOH afforded the desired amine as a light yellow solid in 66.7% yield; m.p. 181°–183° C.

Anal. Calc'd for $C_{14}H_{11}N_3O_2$: C, 66.39; H, 4.37; N, 16.59; Found: C, 66.38; H, 4.34; N, 16.46

EXAMPLE 7

Preparation of 1-[o-(2,3-dimethylphenylamino)benzoyl]-1H-indazol-3-ol

1H-Indazol-3-ol was reacted with N-(2,3-dimethylphenyl)isatoic anhydride according to the general procedure A above and afforded the desired amine as a yellow solid in 42.5% yield; m.p. 182°–184° C.

Anal. Calc'd for $C_{22}H_{19}N_3O_2$: C, 73.93; H, 5.36; N, 11.76; Found: C, 73.80; H, 5.41; N, 11.68

EXAMPLE 8

Preparation of 1-[o(3-Trifluoromethylphenylamino)benzoyl]-1H-indazol-3-ol

1H-Indazol-3-ol was reacted with N-(3-trifluoromethylphenyl)isatoic anhydride according to the general procedure A above and afforded the desired amine as a colorless solid in 16.2% yield; m.p. 177°–179° C.

Anal. Calc'd for $C_{21}H_{14}F_3N_3O_2$: C, 63.48; H, 3.55; F, 14.34; N, 10.57; Found: C, 63.42; H, 3.53; F, 14.36; N, 10.59

EXAMPLE 9

Preparation of 1-(2-Methylamino-4-chlorobenzoyl)-1H-indazol-3-ol

1H-Indazol-3-ol was reacted with N-methyl-4-chloroisatoic anhydride according to the general procedure A above and afforded the desired amine as a yellow solid in 53.5% yield; m.p. 209°–211° C.

Anal. Calc'd for $C_{15}H_{12}ClN_3O_2$: C, 59.71; H, 4.00; Cl, 11.74; N, 13.92; Found: C, 59.81; H, 4.02; Cl, 12.02; N, 13.92

EXAMPLE 10

Preparation of 1-(2-Methylamino-5-chlorobenzoyl)-1H-indazol-3-ol

1H-Indazol-3-ol was reacted with N-methyl-5-chloroisatoic anhydride according to the general procedure A above and afforded the desired amine as a yellow solid in 33.5% yield; m.p. 210°–213° C.

Anal. Calc'd for $C_{15}H_{12}ClN_3O_2$: C, 59.71; H, 4.00; Cl, 11.74; N, 13.92; Found: C, 59.93; H, 4.23; Cl, 11.59; N, 14.00

EXAMPLE 11

Preparation of 1-(2-Methylamino-5-methylbenzoyl)-1H-indazol-3-ol

1H-Indazol-3-ol was reacted with N-methyl-5-methylisatoic anhydride according to the general procedue A above and afforded the desired amine as yellow solid in 40.5% yield; m.p. 173°–175° C.

Anal. Calc'd for $C_{16}H_{15}N_3O_2$: C, 68.31; H, 5.37; N, 14.93; Found: C, 68.24; H, 5.23; N, 14.89

EXAMPLE 12

Preparation of 1-(2-Methylamino-5-methoxybenzoyl)-1H-indazol-3-ol

1H-Indazol-3-ol was reacted with N-methyl-5-methoxy isatoic anhydride according to the general procedure A above and afforded the desired amine as a yellow solid in 40.6% yield; m.p. 161°–163° C.

Anal. Calc'd for $C_{16}H_{15}N_3O_3$: C, 64.63; H, 5.08; N, 14.13; Found: C, 64.21; H, 5.06; N, 13.79

EXAMPLE 13

Preparation of 1-(2-Methylamino-5-nitrobenzoyl)-1H-indazol-3-ol

1H-Indazal-3-ol was reacted with N-methyl-5-nitroisatoic anhydride according to the general procedure A above and afforded the desired amine as a yellow solid in 31.5% yield; m.p. 213°–216° C.

EXAMPLE 14

Preparation of 1-(2-Methylamino-5-aminobenzoyl)-1H-indazol-3-ol

To 1.1 g. of 1-(2-methylamino-5-nitrobenzoyl)-1H-indazol-3-ol, prepared in Example 14, suspended in 200 ml of absolute EtOH was added 200 mg of 5% Pd/C and the mixture was hydrogenated at 50 psi for 16 hours. The catalyst was filtered off, washed with hot EtOH and the filtrate was diluted with $H_2O$ and concentrated to small volume. The precipitate was collected, washed with cold 95% EtOH and dried; yield of dark-yellow amorphous powder 0.65 g. (65.4%); m.p. 184°–186° C.

Anal Calc'd for $C_{15}H_{14}N_4O_2$: C, 63.82; H, 4.99; H, 19.84; Found: C, 64.42; H, 5.27; N, 19.16

EXAMPLE 15

Preparation of 1-(m-Aminobenzoyl)-1H-indazol-3-ol

To 16.0 (0.118 mol) of 1H-indazol-3-ol dissolved in 120 ml of dry pyridine was added 21.8 g (0.118 mol) of m-nitrobenzoyl chloride. The heterogeneous yellow mixture was heated at 95° C. for 2½ hrs. then let cool to room temperature and poured onto 1 liter of ice/$H_2O$. The light yellow precipitate was collected, washed well with $H_2O$ and air-dried. Recrystallization from aqueous EtOH afforded 12.7 g (27.9%) of 1-(m-nitrobenzoyl)-1H-indazol-3-ol as a colorless solid, mp 232°–234° C.

Anal. calcd. for $C_{14}H_9N_3O_4$: C, 59.36; H, 3.20; N, 14.83; Found: C, 59.10; H, 3.24; N, 14.68

Catalytic reduction (5% Pd/C) of the above m-nitro derivative as in Example 14 aboved afforded the 1-(m-aminobenzoyl)1H-indazol-3-ol as a colorless solid in 33.2% overall yield; mp 188°–190° C.

Anal. calcd. for $C_{14}H_{11}N_3O_2$: C, 66.39; H, 4.37; N, 16.59; Found: C, 66.42; H, 4.42; N, 16.65

EXAMPLE 16

Preparation of 1-(p-Aminobenzoyl)-1H-indazol-3-ol

Reaction of 1H-indazol-3-ol with p-nitrobenzoyl chloride and subsequent catalytic reduction of the nitrobenzoyl indazol derivative according to the general procedure B above afforded the desired amine as a colorless solid in 49.1% overall yield; m.p. 233°–235° C.

Anal. Calc'd for $C_{14}H_{11}N_3O_2$: C, 66.39; H, 4.37; N, 16.59; Found: C, 66.55; H, 4.32; N, 16.46

EXAMPLE 17

Preparation of 1-(o-Methylaminobenzoyl)-6-chloro-1H-indazol-3-ol

6-Chloro-1H-indazol-3-ol was reacted with N-methylisatoic anhydride according to the general procedure A above and afforded the desired amine as a yellow solid in 59.0% yield; m.p. 203°–205° C.

Anal. Calc'd for $C_{15}H_{12}ClN_3O_2$: C, 59.71; H, 4.00; Cl, 11.74; N, 13.92; Found: C, 59.62; H, 3.90; Cl, 12.04; N, 13.90

EXAMPLE 18

Preparation of 1-(o-Methylaminobenzoyl)-5-chloro-1H-indazol-3-ol

5-Chloro-1H-indazol-3-ol was reacted with N-methylisatoic anhydride according to the general procedure A above and afforded the desired amine as a yellow solid in 32.3% yield; m.p. 206°–208° C.

Anal. Calc'd for $C_{15}H_{12}ClN_3O_2$: C, 59.71; H, 4.00; Cl, 11.74; N, 13.92; Found: C, 59.87; H, 3.85; Cl, 12.01; N, 14.00

EXAMPLE 19

Preparation of 1-(o-Methylaminobenzoyl)-5-nitro-1H-indazol-3-ol

5-Nitro-1H-indazol-3-ol was reacted with N-methylisatoic anhydride according to the general procedure A above and afforded the desired amine as an orange solid in 47.0% yield; m.p. >270° C.

Anal. Calc'd for $C_{15}H_{12}N_4O_4$: C, 57.69; H, 3.87; N, 17.94; Found: C, 57.29; H, 3.94; N, 17.85

EXAMPLE 20

Preparation of 1-(o-Methylaminobenzoyl)-5-amino-1H-indazol-3-ol

To 1.5 g. of 1-(2-methylaminobenzoyl)-5-nitro-1H-indazol-3-ol, prepared in Example 19, suspended in 500 ml. of absolute EtOH was added 1.0 g. of 5% Pd/C and the mixture was hydrogenated at 50 psi for 20 hours. The catalyst was filtered off, washed with absolute EtOH and the filtrate evaporated to afford a semi-solid. Recrystallization from EtOH afforded 0.48 g. (35.4%) of the amine as a tan amorphous powder; mp. 169°–170° C.

Anal. Calc'd for $C_{15}H_{14}N_4O_2$: C, 63.82; H, 4.99; N, 19.84; Found: C, 63.73; H, 5.20; N, 19.71

EXAMPLE 21

Preparation of 1-(o-Methylaminobenzoyl)-5-methoxy-1H-indazol-3-ol

5-Methoxy-1H-indazol-3-ol was reacted with N-methylisatoic anhydride according to the general procedure A above and afforded the desired amine as a yellow solid in 67.0% yeild; m.p. 175°–177° C.

Anal. Calc'd for $C_{16}H_{15}N_3O_3$: C, 64.63; H, 5.08; N, 14.13; Found: C, 64.59; H, 5.00; N, 14.10

EXAMPLE 22

Preparation of 3-Methoxy-1-(o-methylaminobenzoyl)-1H-indazole (A) 3-Methoxy-1H-indazole was reacted with N-methylisatoic anhydride according to the general procedure A above and afforded the desired amine as a yellow solid in 31.4% yield; m.p. 96°–97° C.

Anal. Calc'd for $C_{16}H_{15}N_3O_2$: C, 68.31; H, 5.37; N, 14.93; Found: C, 68.18; H, 5.50; N, 15.08

(B) To 50.g (0.019 mol) of 1-(o-methylaminobenzoyl)-1H-indazol-3-ol dissolved in 200 ml of acetone was added 2.6 g (1 equiv.) of $K_2CO_3$ followed by 1.2 ml of $CH_3I$ (Procedure C). The yellow mixture was allowed to stir at reflux for 16 hours, cooled to room temperature and filtered. The filtrate was evaporated at reduced pressure. The residual oil taken up in $CHCl_3$, the organic solution washed with water, dried, and evaporated. Chromatography on silica gel using $CHCl_3$ as eluent afforded 2.5 g of the desired o-methyl product, m.p. 96°–97° C. as well as 2.6 g of the N-methylated by-product, 1-o-methylaminobenzoyl)-1,2-dihydro-2-methylindazolin-3-one, m.p. 152°–154° C.

Anal. Calc'd for $C_{16}H_{15}N_3O_2$: C, 68.31; H, 5.37; N, 14.93; Found: C, 68.18; H, 5.50; N, 15.08

EXAMPLE 23

Preparation of 3-Hydroxy-1-(o-methylaminobenzoyl)-1H-pyrazolo[4,3-b]pyridine

Pyrazolo[4,3-b]pyridine-3(2H)-one was reacted with N-methylisatoic anhydride according to the general procedure A above and afforded the desired amine as a yellow solid in 84.8% yield; m.p. 221°–223° C., Anal. Calc'd for $C_{14}H_{12}N_4O_2$: C, 62.67; H, 4.50; N, 20.88; Found: C, 62.43; H, 4.46; N, 20.87

Established methods were employed for demonstrating the anti-inflammatory activity of certain of the compounds of the invention and consisted of the following: the carrageenan-induced paw edema assay of Winter [*Proc. Soc. Exp. Biol.*, 111, 544 (1962)]. In this test, anti-inflammatory activity is determined as the inhibition of edema formation in the hind paw of male Sprague-Dawley rats (weight 160–200 g) in response to the subplantar injection of carrageenan. The carrageenan is injected as a 1% aqueous suspension (0.1 ml) 2 hours after oral (drug dissolved or suspended in a 0.5% water solution of methocel) administration of the drug. The volume of the paw is measured plethometrically immediately following carrageenan administration and 3 hours later. The increase in volume 3 hours after carrageenan injection constitutes the individual response. Drug effects are calculated as a percent inhibition of the swelling, taking the swelling of the control group as 100%. In the carrageenan induced rat paw edema test anti-inflammatory activity is produced by the compounds of this invention at oral doses of about 25–100 mg/kg. For example, the compound 1-(o-methylaminobenzoyl)-1H-indazol-3-ol prepared in Example 1 gave about a 45% inhibition of edema at a 25 mg/kg oral dosage and the compound 1-(o-aminobenzoyl)-1H-indazol-3-ol prepared in Example 6 gave about a 40% inhibition of edema at a 25 mg/kg oral dosage. Other compounds of the invention showed anti-inflammatory and/or immunomodulatory activity.

I claim:

1. An aminobenzoyl-1H-indazole-3-ol having the formula:

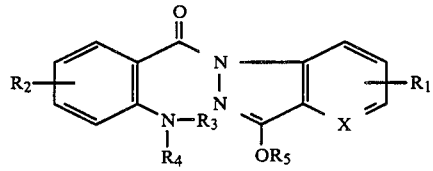

in which $R_1$ and $R_2$ are independently selected from the group consisting of H, lower alkyl, lower alkoxy, hydroxy, amino, nitro, and halogen, $R_3$ is selected from the group consisting of H, lower alkyl, cycloalkyl having 3 to about 7 carbons, phenyl, phenyl which is mono- or disubstituted with lower aryl or trifluoromethyl, and benzyl, $R_4$ is H and $R_5$ is selected from H and lower alkyl, and X is CH or N, or a pharmacologically acceptable salt thereof.

2. A pharmacologically acceptable salt of the compound as claimed in claim 1.

3. A compound according to claim 1 wherein the compound is 1-(o-aminobenzoyl)-1H-indazol-3-ol.

4. A compound according to claim 1 wherein the compound is 1(o-methylaminobenzoyl)-1H-indazol-3-ol.

5. A compound according to claim 1 wherein the compound is 1-(o-ethylaminobenzoyl)-1H-indazol-3-ol.

6. A compound according to claim 1 wherein the compound is 1-(o-isopropylaminobenzoyl)-1H-indazol-3-ol.

7. A compound according to claim 1 wherein the compound is 1-(o-cyclohexylaminobenzoyl)-1H-indazol-3-ol.

8. A compound according to claim 1 wherein the compound is 1-(o-benzylaminobenzoyl)-1H-indazol-3-ol.

9. A compound according to claim 1 wherein the compound is 1-[o-(2,3-dimethylphenylamino)benzoyl]-1H-indazol-3-ol.

10. A compound according to claim 1 wherein the compound is 1-[o(3-trifluoromethylphenylamino)benzoyl]-1H-indazol-3-ol.

11. A compound according to claim 1 wherein the compound is 1-(2-methylamino-4-chlorobenzoyl)-1H-indazol-3-ol.

12. A compound according to claim 1 wherein the compound is 3-methoxy-1-(o-methylaminobenzoyl)-1H-indazole.

13. A compound according to claim 1 wherein the compound is 3-hydroxy-1-(o-methylaminobenzoyl)-1H-pyrazolo[4,3-b]pyridine.

14. A compound according to claim 1 wherein the compound is 1-(2-methylamino-5-methylbenzoyl)-1H-indazol-3-ol.

15. A compound according to claim 1 wherein the compound is 1-(2-methylamino-5-methoxybenzoyl)-1H-indazol-3-ol.

16. A compound according to claim 1 wherein the compound is 1-(o-methylaminobenzoyl)-6-chloro-1H-indazol-3-ol.

17. A compound according to claim 1 wherein the compound is 1-(o-methylaminobenzoyl)-5-amino-1H-indazol-3-ol.

18. A compound according to claim 1 wherein the compound is 1-(o-methylaminobenzoyl)-5-nitro-1H-indazol-3-ol.

* * * * *

UNITED STATES PATENT AND TRADEMARK OFFICE
CERTIFICATE OF CORRECTION

PATENT NO. : 4,537,966

DATED : August 27, 1985

INVENTOR(S) : Robert J. Murray

Page 1 of 2

It is certified that error appears in the above-identified patent and that said Letters Patent are hereby corrected as shown below:

In column 2 at line 35 the structural formula should be as follows:

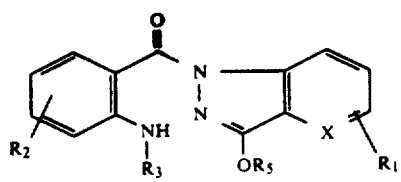

In column 2 at line 65 the structural formula should be as follows:

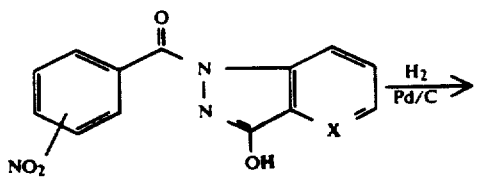

UNITED STATES PATENT AND TRADEMARK OFFICE
CERTIFICATE OF CORRECTION

PATENT NO. : 4,537,966

DATED : August 27, 1985

INVENTOR(S) : Robert J. Murray

It is certified that error appears in the above-identified patent and that said Letters Patent are hereby corrected as shown below:

In column 3 at line 25 the structural formula should be as follows:

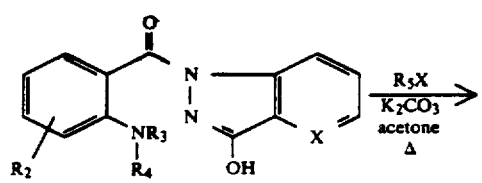

In claim 1 line 61 "aryl" should read --alkyl--.

Signed and Sealed this

Nineteenth Day of July, 1988

*Attest:*

DONALD J. QUIGG

*Attesting Officer*  *Commissioner of Patents and Trademarks*